United States Patent
Doerr

(10) Patent No.: US 8,644,920 B2
(45) Date of Patent: Feb. 4, 2014

(54) IMPLANTABLE MEDICAL DEVICE HAVING MAGNETIC RESONANCE TOMOGRAPHY ANTENNA

(75) Inventor: Thomas Doerr, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 316 days.

(21) Appl. No.: 12/958,423

(22) Filed: Dec. 2, 2010

(65) Prior Publication Data

US 2011/0152674 A1    Jun. 23, 2011

Related U.S. Application Data

(60) Provisional application No. 61/288,854, filed on Dec. 22, 2009.

(51) Int. Cl.
*A61B 5/00* (2006.01)

(52) U.S. Cl.
USPC ............... 607/2; 600/411; 607/5; 607/9

(58) Field of Classification Search
USPC ......... 600/409, 410, 417, 421, 422, 423, 425; 606/130; 324/307, 309, 318
See application file for complete search history.

(56) References Cited

U.S. PATENT DOCUMENTS

| | | | |
|---|---|---|---|
| 6,101,417 A | 8/2000 | Vogel et al. | |
| 7,164,950 B2 | 1/2007 | Kroll et al. | |
| 7,242,981 B2 * | 7/2007 | Ginggen | 607/27 |
| 8,019,419 B1 * | 9/2011 | Panescu et al. | 607/33 |
| 8,108,028 B2 * | 1/2012 | Karmarkar | 600/423 |
| 8,543,207 B2 * | 9/2013 | Cooke et al. | 607/31 |
| 2003/0144704 A1 | 7/2003 | Terry et al. | |
| 2004/0088012 A1 | 5/2004 | Kroll et al. | |
| 2006/0214662 A1 * | 9/2006 | Adachi | 324/322 |
| 2006/0293591 A1 | 12/2006 | Wahlstrand et al. | |
| 2008/0154342 A1 | 6/2008 | Digby et al. | |
| 2008/0183097 A1 * | 7/2008 | Leyde et al. | 600/545 |
| 2011/0152672 A1 * | 6/2011 | Doerr et al. | 600/421 |
| 2011/0152673 A1 * | 6/2011 | Doerr et al. | 600/421 |
| 2012/0161901 A1 * | 6/2012 | Stevenson et al. | 333/175 |
| 2012/0277638 A1 * | 11/2012 | Skelton et al. | 600/595 |
| 2013/0053716 A1 * | 2/2013 | Zhang et al. | 600/513 |

FOREIGN PATENT DOCUMENTS

| | | |
|---|---|---|
| EP | 1935450 | 6/2008 |
| WO | WO 96/41203 | 12/1996 |

OTHER PUBLICATIONS

European Search Report Dated Apr. 5, 2011 (7 pages).
European Search Report dated Aug. 30, 2011 (13 pages).

* cited by examiner

*Primary Examiner* — Unsu Jung
*Assistant Examiner* — Amanda Lauritzen Moher
(74) *Attorney, Agent, or Firm* — ARC IP Law, PC; Joseph J. Mayo

(57) ABSTRACT

The disclosure relates to a device and a method for detecting electromagnetic fields, in particular fields occurring in imaging magnetic resonance tomography.

14 Claims, 4 Drawing Sheets

IMPLANTABLE MEDICAL DEVICE HAVING MAGNETIC RESONANCE TOMOGRAPHY ANTENNA

RELATED APPLICATION

This patent application claims the benefit of U.S. Provisional Patent Application No. 61/288,854, filed on Dec. 22, 2009, which is hereby incorporated by reference in its entirety.

TECHNICAL FIELD

The disclosure relates to a device and a method for detecting electromagnetic fields, in particular fields occurring in magnetic resonance tomography (referred to below as "MRT" and magnetic resonance imaging as "MRI") devices.

BACKGROUND

Although MRI testing is becoming increasingly important in diagnostic medicine, it is contraindicated for some patients. Such contraindication may result from an active implanted medical device (also referred to below as "implant" or "IMD"). Besides MRI testing, however, other technical applications pose a risk to the user of medical devices or implantable medical devices, particularly when such applications generate strong electromagnetic interference (EMI) fields in their surroundings.

In order to still allow MRI testing, various approaches are known which relate either to performing the MRI testing or to the implantable medical device.

Among others, technologies based on conventional processes for identifying magnetic fields are known for detecting magnetic fields. U.S. 2008/0154342 describes a method which uses a giant magnetoresistance (GMR) sensor to detect problematic magnetic fields from MRT devices. In addition, U.S. Pat. No. 7,164,950 describes an approach for detecting interference fields typical for MRT, the object of which is to detect radio frequency (RF) fields by use of additional antennas, although in this respect an additional sensor is always necessary for detecting magnetic fields. Thus, the system described in the prior art has several disadvantages, such as the deactivation of relevant functions, for example antibradycardial stimulation, the presence of filtered and unfiltered passages into the implant, and the required adjustment of the RF detector using a magnetic field sensor.

What is needed is a way to provide a simple and reliable device and method for detecting typical MRT fields.

SUMMARY

The object is achieved by an implantable medical device (IMD) and method as claimed, in which the IMD is equipped with an MRT interference detection unit.

The disclosed IMD comprises at least the following:
a hermetically sealed housing;
at least one control unit;
at least one power supply;
at least one RF antenna, and at least one RF communication unit, the RF communication unit in conjunction with the RF antenna being designed to allow communication between an external programming device and the IMD;
an MRT interference detection unit having a demodulation unit;
an MRT interference detection unit which is connected at least to the RF communication unit, or to the RF antenna, or to both the RF communication unit and the RF antenna by means of at least one frequency diplexer, such that the demodulation unit detects the RF rotary fields typical for MRT and transmits an MRT detection signal from the MRT detection unit to at least one control unit.

In a preferred embodiment the RF antenna is designed for communication in the medical implant communication service (MICS) band and/or the industrial, scientific, and medical (ISM) band.

It is also preferred that when MRT is detected, a notation is made in a diagnostic memory, and/or no episodes are recorded during an MRT test. This prevents an MRT session from overwriting the diagnostic data with artifacts.

The IMD is preferably a cardiac pacemaker, an implanted cardioverter/defibrillator (ICD), a cardiac resynchronization therapy (CRT) device, a neurostimulator, or an implant for monitoring physiological signals, such as but not limited to an implanted cardiac monitor. In a further preferred embodiment, the MRT detection is based on an evaluation of the frequency spectrum, typical for MRT, at the antenna.

In one preferred variant the magnetic field intensities typical for various types of devices are associated with typical frequencies. For the typical frequencies this results in a parameter space from approximately 64 MHz for 1.5-tesla devices to 300 MHz for 7.0-tesla devices.

It is also preferred that the MRT interference detection unit is additionally connected and/or connectable via a frequency diplexer to an electrode line that is present, and MRT detection occurs only when RF rotary fields are simultaneously detected via the antenna and via the electrode line.

It is also preferred that the antenna diagram of the RF antenna has maxima in three spatial directions, preferably in three orthogonal spatial directions. In this manner a rotary field may be differentiated from a pulsed alternating field in the demodulation unit. For this purpose, in addition to a typical RF antenna, further RF antennas may be present in order to achieve a high level of confidence in the differentiation between rotary fields and pulsed alternating fields.

It is also preferred that a change is made to an MRT-safe state when a field typical for MRT is detected, this state being either permanent until a possible reprogramming, or temporary for a specified period of time, or being maintained until there is no MRT detection or until there is no MRT detection for a specified period of time. This also includes logical linkages of the referenced time periods for maintaining the MRT-safe state, in particular combinations in which a respective earliest or latest event specifies the time period. The rules for maintaining the MRT-safe state are or may be predetermined Predetermination based on the patient and on testing may ensure optimum operation of the IMD for the particular patient without exposing the device and/or the patient to additional risks from the MRT testing.

In a further preferred embodiment the IMD is an implantable stimulator, such as but not limited to a cardiac pacemaker, ICD, or neurostimulator, and the MRT-safe state has a fixed stimulation rate, such as but not limited to V00, A00, or generally asynchronous or 000, or a specified or predetermined stimulation characteristic, and/or the delivery of high-energy stimuli is inhibited for an ICD, and/or tachycardial detection is inhibited. The terms 000, V00, D00, and A00 refer to modes in which there is no stimulation, or in which there is stimulation in the ventricle, or in the ventricle and atrium, or in the atrium. These terms are commonly used in the literature.

It is also preferred that the MRT interference detection unit performs MRT detection only before or during charging of a high-voltage capacitor.

It is further preferred that during the MRT detection the antenna is tuned to the RF frequency spectra that are typical for MRT, it being possible to specify a fixed frequency or to sample one or more frequency ranges.

In particular, the typical frequency ranges are preferably between 64 MHz for 1.5-tesla MRT devices and 300 MHz for 7.0-tesla devices, although the frequency ranges may also be expanded to other ranges, in particular when other magnetic field intensities are used.

It is also preferred that the sampling of one or more frequency ranges is carried out using one or more band pass filters, or programmable band pass filters.

In a further preferred embodiment, for MRT devices which operate at different magnetic field intensities and thus different RF frequencies, different predetermined MRT-safe states are automatically selected.

It is also preferred that the IMD is switched to an MRT-safe state when the MRT interference detection unit has detected an MRT field, and that the MRT-safe state has VF detection which may be prolonged by a predetermined period of time in order to provide a reliable differentiation between normal RF interferences and interferences from MRT. In this context, the term "VF" (venticular fibrillation) refers to all rapid disturbances in cardiac rhythm, and for each patient an individual, appropriate cutoff frequency must be assumed and/or specified, or a predetermined cutoff frequency is selected. Thus, VF stands for the sensing and classification of a persistent tachycardial ventricular rhythm disturbance, which is generally classified as requiring therapy, and is treated by means of antitachycardial stimulation or defibrillation shock therapy of the ICD.

It is particularly preferred that the MRT interference detection unit is also connected to further indicators for MRT interference fields or to at least one MRT sensor. The MRT detection is based on identification by at least one of the sensors or indicators. In the context of the present patent application, "MRT sensor" or "MRT indicator" is understood to mean, in addition to the MRT detection, any sensor or device or component which allows detection of MRT fields or other strong electromagnetic fields. These include but are not limited to GMR sensors, MagFET sensors, Hall sensors, monitoring of battery voltages during capacitor charging processes, detection of gradient fields, detection of currents induced by electromagnetic fields, detection by light-emitting diodes which are excited to emit light by MRT fields, and detection of specific vibrations, or components designed as sensors for detection of vibrations induced by Lorentz forces. In addition, a position sensor, in particular a self-calibrating position sensor, may be used to increase the specificity of the MRT detection.

It is further preferred that a position sensor is used for plausibility checking, and a positive MRI identification is made only when the position sensor reports a prone posture and/or another presettable posture.

The position sensor is particularly preferably self-calibrating, the calibration taking place under presettable boundary conditions such as, but not limited to, times of day, heart rate, respiratory rate, hemodynamic parameters, and activity detected by a motion sensor.

It is also preferred that at least one of the following measures is introduced for MRT detection:

Changing to an MRI-safe state;

Remaining for a prolonged period of time in an MRI-safe state or a state that is insensitive to electromagnetic interference fields;

Synchronization of electrical measurements (impedance measurements, for example) using field intensity minimum values occurring with periodic or pulsed electromagnetic fields, or synchronization of a stimulation using these same minimum values; and Emission of electromagnetic pulses for signaling that a medical device, in particular an implant, is present in the electromagnetic field, in particular for signaling to an MRI device, with the possibility of thus transmitting information as well as the interference and displaying same on the MRT screen.

A method for detecting electromagnetic interferences, generated by MRT devices, in an implantable medical device (IMD) provides that RF rotary fields emitted by MRT may be detected by the IMD by means of an RF antenna and an RF communication unit, and an MRT detection unit which may be connected to an RF communication unit and having a demodulation unit detects the RF fields emitted by MRT, and thereupon transmits an MRT detection signal from the MRT detection unit to a control unit.

DETAILED DESCRIPTION

Figure 1:
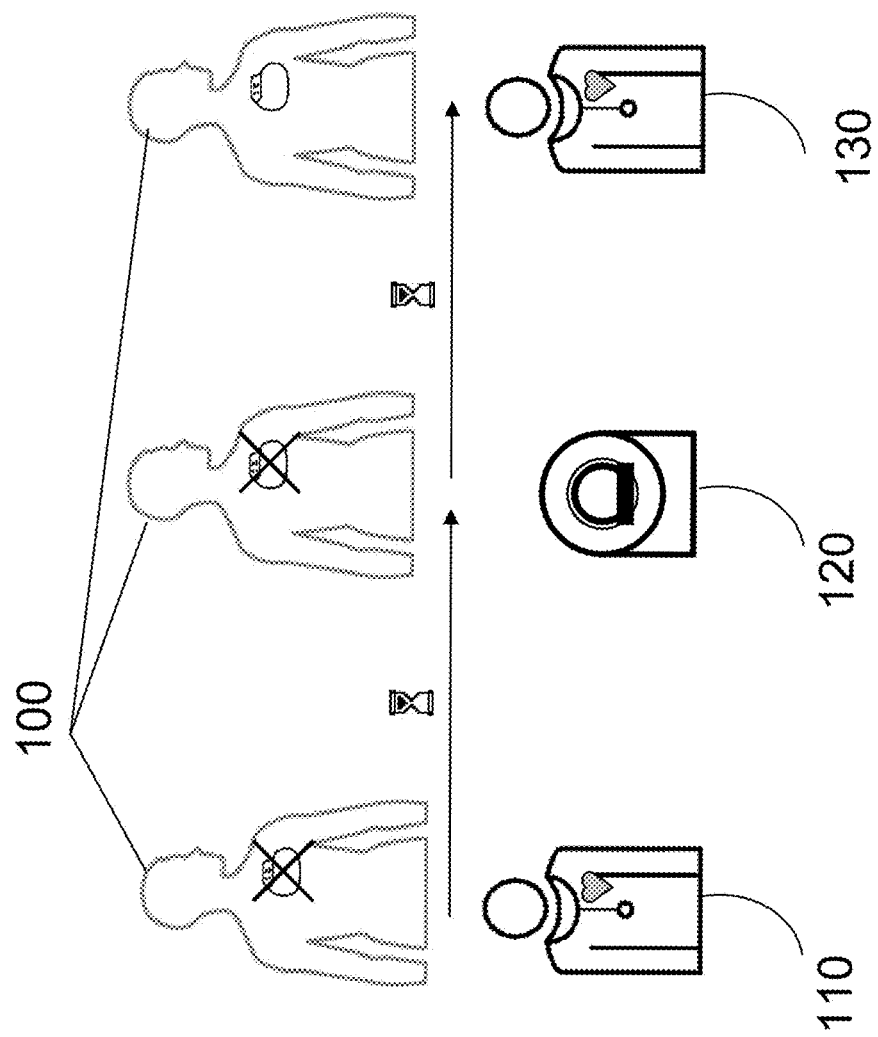
FIG. 1 shows a schematic illustration of the sequence of a prior art MRT test.

FIG. 1 illustrates the starting situation, i.e., the current clinical prior art. An ICD patient 100 receives follow-up care from a first cardiologist 110 before the planned MRT test, at which time the ICD is switched off. After a first time delay of hours to days the MRT test is performed by a radiologist 120. After a further time delay the patient is once again under the care of a second cardiologist 130 (who may or may not be the same as first cardiologist 110), at which time the ICD is switched back on. During the two time delay intervals, the patient 100 is without the protection of the implanted defibrillator, and is essentially without rhythm monitoring. This residual risk is currently accepted in return for the benefits of the MRT test. In addition, the economic and logistic expenditure for such a procedure is very high, and in many cases rules out emergency use of MRT. The procedure is similar to that for pacemaker patients and patients having other implants, wherein the devices do not necessarily have to be placed in an inhibited mode; instead, other operating modes may be used, depending on the individual patient. However, all the processes have the common feature that before, during, and after the MRT test the patient is not provided with optimal care.

Figure 2:
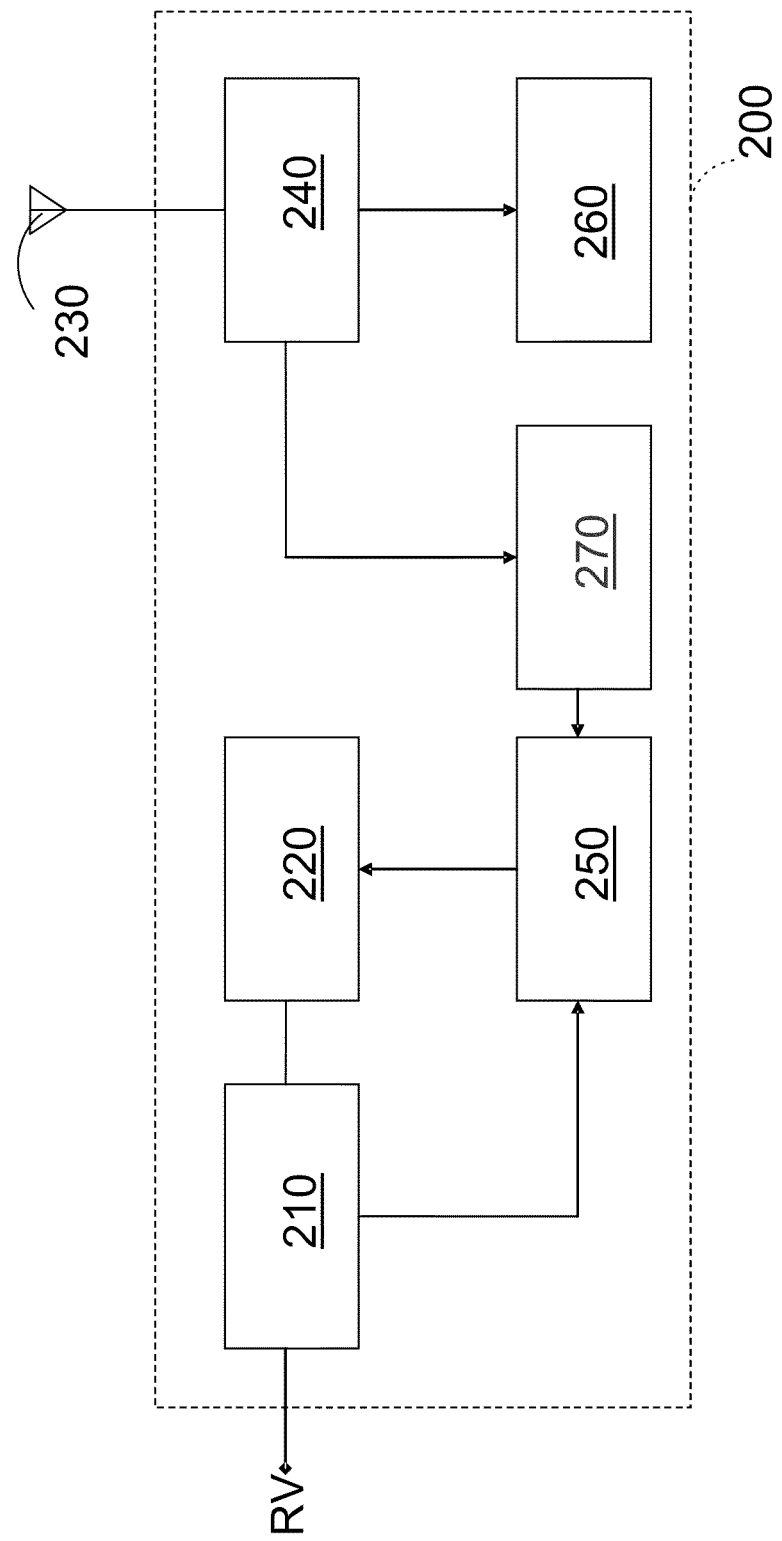
FIG. 2 shows a block diagram of an IMD together with one embodiment of an MRT interference detection unit.

FIG. 2 shows a block diagram of a novel approach for detecting the MRT interference field in tan electronic implant 200, using the example of an ICD (An IPG, neurostimulators, medication pumps, or the like are also possible). A right ventricular (RV) electrode used for detecting ventricular fibrillation (VF) is connected to an electrocardiogram (EKG) unit 210 for signal sensing/rhythm classification and stimulation. This unit is in turn connected to a treatment control unit 220 which selects the appropriate stimulation therapy corresponding to the rhythm classification. The implant has an RF antenna 230 for communication with the programming device. The RF antenna 230 is connected to an RF telemetry communication unit 260 on the one hand and to an interference signal detector 250 on the other hand via a frequency diplexer 240. This interference signal detector 250 is also connected to the EKG signal sensing unit 210. The interference signal detector 250 is designed in such a way that the simultaneous occurrence of high-frequency signal components at the electrode (RV) and at the RF antenna 230 may be differentiated from high-frequency signals at only one signal source. The high frequency of the RF antenna is tuned to the typical frequencies of the MRT by means of band pass filtering, and is then sent to the rotary field demodulator 270. This rotary field demodulator 270 sends an output signal whenever the modulation that is typical for the rotary field has been demodulated and classified (amplitude demodulation, for example). When the interference signal detector 250 senses simultaneous onset of the interference at the electrode (RV) and a detected rotary field at the antenna 230, it signals to the control unit 220 the probable presence of MRT in the surroundings of the implant 200. In this case, the control unit 220 automatically sets a previously specified (programmed) parameter combination for safe operation within an MRT device (for example, V00 mode and VF detection off).

One alternative implementation of the MRT interference signal detector 250 also evaluates the amplitude of the band pass-filtered interference signal from the RF antenna 230 in the predefined typical frequency range of MRT.

Figure 3:
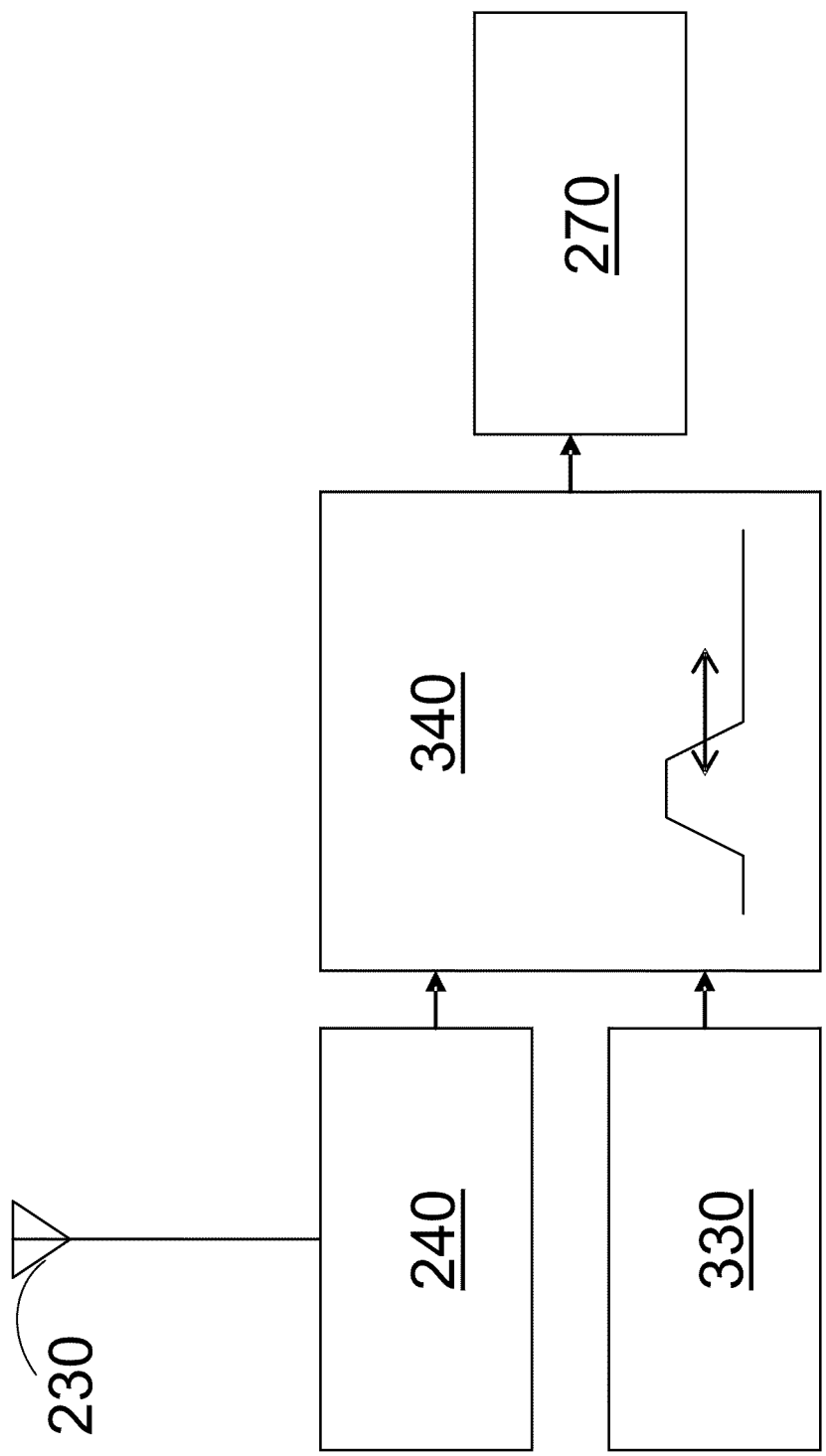
FIG. 3 shows a block diagram of an IMD together with a first alternative embodiment of an MRT interference detection unit, implemented with a programmable bandpass filter.

FIG. 3 illustrates an expansion of the block diagram shown in FIG. 2. In this case the RF antenna 230 is again connected to a frequency diplexer 240. The output signal thereof for the MRT RF field detection is sent to a programmable bandpass filter 340. This programmable filter 340 may be reprogrammed with respect to the cutoff frequencies by means of a filter control unit 330, thus allowing a sequential scan of possible frequency ranges of various MRT systems (for example, from 1.5 T . . . 7 T=~64 MHz . . . ~298 MHz). The output of the programmable filter 340 is always connected to the rotary field demodulator 270.

Figure 4:
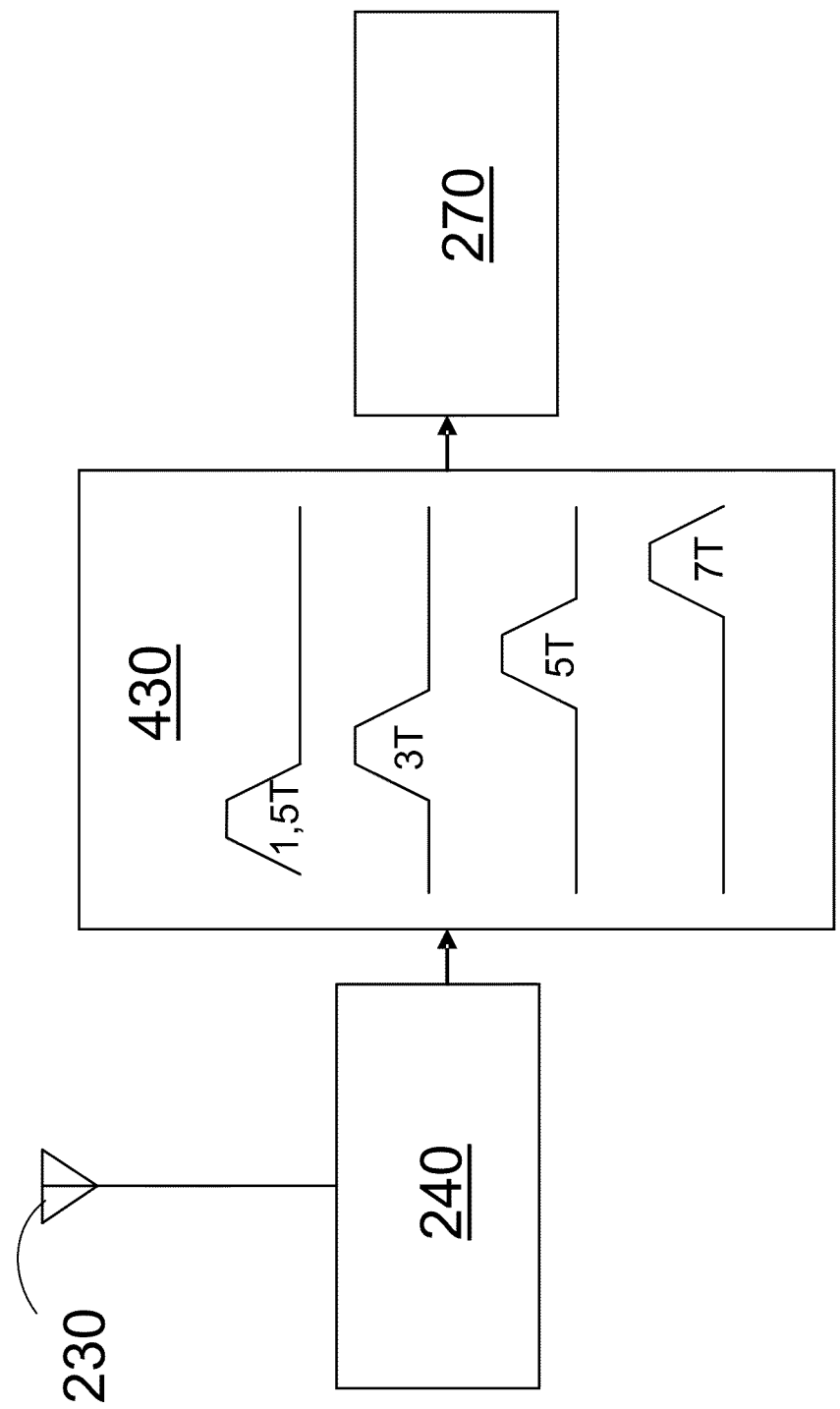
FIG. 4 shows a block diagram of an IMD together with a second alternative embodiment of an MRT interference detection unit, implemented with a multichannel filter.

FIG. 4 shows an alternative embodiment that includes the optional use of a multichannel filter 430. In this case, the RF antenna 230 is connected to the multichannel filter 430 via a frequency diplexer 240. The multichannel filter 430 is designed in such a way that it contains one band pass for each common MRT RF frequency. The output of this filter 430 is always connected to the rotary field demodulator 270. To avoid nonspecific deactivation of the VF detection over an extended period of time, the interference signal detection may optionally be limited to a given time window by means of programming Thus, for a planned MRT test the MRT interference detection, for example, may be activated for several days by means of programming. After this time has elapsed, the interference detection may be automatically deactivated so that, referring back to FIG. 1, reprogramming by second cardiologist 130 is not necessary.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. An implantable medical device (IMD), comprising:
   a hermetically sealed housing,
   at least one control unit,
   at least one power supply,
   at least one RF antenna, and
   at least one RF communication unit, wherein the RF communication unit in conjunction with the at least one RF antenna are configured to allow communication between an external programming device and the implantable medical device;
   at least one frequency diplexer;
   a magnetic resonance tomography (MRT) interference detection unit having a demodulation unit, wherein the MRT interference detection unit is connected to
      said at least one RF communication unit or
      said at least one RF antenna or
      said at least one RF communication unit and said at least one RF antenna, by said at least one frequency diplexer;
   wherein said demodulation unit is configured to detect RF rotary fields typical of MRT and transmit an MRT detection signal from the MRT detection unit to the at least one control unit; and,
   wherein the MRT interference detection unit is additionally connected or connectable via one of said at least one frequency diplexer to an electrode line that is present, and wherein the demodulation unit is configured to detect the MRT only when RF rotary fields are simultaneously detected via the at least one RF antenna and via the electrode line.

2. The IMD according to claim 1, wherein the at least one RF antenna is configured to communicate in a medical implant communication service (MICS) frequency band.

3. The IMD according to claim 1, wherein the at least one RF antenna is configured to communicate in at least one of an industrial, scientific, and medical (ISM) band.

4. The IMD according to claim 1, wherein the demodulation unit is configured to detect the MRT based on an evaluation of a frequency spectrum typical for that MRT, that occurs at the at least one RF antenna.

5. The IMD according to claim 1, wherein the at least one RF antenna has maxima in three spatial directions, preferably in three orthogonal spatial directions.

6. The IMD according to claim 1, wherein the IMD is switched to an MRT safe state when the MRT interference detection unit has detected an MRT field, and the MRT-safe state has ventricular fibrillation (VF) detection which may be prolonged by a predetermined period of time.

7. The IMD according to claim 1, wherein the MRT interference detection unit is further connected to indicators configured to indicate MRT interference fields or to at least one MRT sensor.

8. The IMD according to claim 1, wherein the at least one control unit is configured, in case of MRT electromagnetic field detection, to:
   change to an MRI-safe state;
   remain for a prolonged period of time in an MRI-safe state;
   remain for a prolonged period of time in a state that is otherwise insensitive to electromagnetic interference fields;
   synchronize electrical measurements with field intensity minimum values that occur with periodic or pulsed electromagnetic fields;

synchronize a stimulation using the minimum values; or
emit electromagnetic pulses configured to signal that a medical device, or an implant, is present in the MRT electromagnetic field.

9. The IMD according to claim 1, wherein a change is made to an MRT safe state when a field typical of the MRT is detected, this state being either permanent until a possible reprogramming, or temporary for a specified period of time, or being maintained until no MRT is detected or until there is no MRT is detected for a specified period of time.

10. The IMD according to claim 9, wherein the IMD is an implantable stimulator, cardiac pacemaker, ICD (implanted cardioverter/defibrillator), or neurostimulator, and the MRT-safe state has a fixed stimulation rate, or a specified or predetermined stimulation characteristic, and/or the delivery of high-energy stimuli is inhibited for the ICD, and/or tachycardial detection is inhibited.

11. The IMD according to claim 1, wherein the MRT interference detection unit performs MRT detection only before or during charging of a high-voltage capacitor.

12. The IMD according to claim 11, wherein during the MRT detection, the at least one RF antenna is tuned to one or more RF frequencies that are typical of the MRT, in order to specify either a fixed frequency or to sample a frequency range.

13. The IMD according to claim 12, wherein the sample of the frequency range comprises a sample of one or more frequency ranges and is carried out using a band pass filter.

14. The IMD according to claim 11, wherein different predetermined MRT-safe states are automatically selected for MRT devices which operate at different magnetic field intensities and thus different RF frequencies.

* * * * *